United States Patent
Jeoung et al.

(10) Patent No.: US 11,858,874 B2
(45) Date of Patent: Jan. 2, 2024

(54) METHOD FOR PREPARING ALPHA-METHYLSTYRENE

(71) Applicant: LG CHEM, LTD., Seoul (KR)

(72) Inventors: Jaekwon Jeoung, Daejeon (KR); Dong Hyun Ko, Daejeon (KR); Sunhwan Hwang, Daejeon (KR); Jun Han Kang, Daejeon (KR); Sang Jin Han, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/761,149

(22) PCT Filed: Aug. 30, 2021

(86) PCT No.: PCT/KR2021/011611
§ 371 (c)(1),
(2) Date: Mar. 16, 2022

(87) PCT Pub. No.: WO2022/139117
PCT Pub. Date: Jun. 30, 2022

(65) Prior Publication Data
US 2023/0034930 A1 Feb. 2, 2023

(30) Foreign Application Priority Data

Dec. 21, 2020 (KR) ........................ 10-2020-0179516

(51) Int. Cl.
*C07C 1/24* (2006.01)
*C07C 15/46* (2006.01)

(52) U.S. Cl.
CPC ............... *C07C 15/46* (2013.01); *C07C 1/24* (2013.01)

(58) Field of Classification Search
CPC .... C07C 1/24; C07C 1/20; C07C 1/00; C07C 15/46; C07C 29/132; C07C 5/11; C07C 7/04; C07C 7/09
See application file for complete search history.

(56) References Cited

U.S. PATENT DOCUMENTS 5,245,090 A 9/1993 Decaria et al.
5,254,751 A 10/1993 Zakoshansky
(Continued)

FOREIGN PATENT DOCUMENTS

CN 105669367 B 9/2017
JP 62164637 A 7/1987
(Continued)

OTHER PUBLICATIONS

Korstanje, et al. (2010).Catalytic Dehydration of Benzylic Alcohols to Styrenes by Rhenium Complexes. ChemSusChem vol. 3, pp. 695-697.

*Primary Examiner* — Sharon Pregler
(74) *Attorney, Agent, or Firm* — Bryan Cave Leighton Paisner LLP

(57) ABSTRACT

A method for preparing alpha-methylstyrene according to one embodiment of the present disclosure includes dehydrating a dimethylbenzyl alcohol solution in a reactor under an acid catalyst to prepare alpha-methylstyrene, where a reaction product after the dehydration reaction comprises a first reaction product including a first alpha-methylstyrene; and a second reaction product including vapor ($H_2O$), a second alpha-methylstyrene and unreacted materials; and separating the second alpha-methylstyrene and the unreacted materials comprised in the second reaction product and recirculating the second alpha-methylstyrene and the unreacted materials to the reactor, a temperature inside the reactor during the dehydration reaction is 135° C. or higher, and a content of the acid catalyst is from 100 ppm to 1,500 ppm based on a total weight of dimethylbenzyl alcohol of the dimethylbenzyl alcohol solution.

7 Claims, 1 Drawing Sheet

(56) References Cited

U.S. PATENT DOCUMENTS

| | | | |
|---|---|---|---|
| 6,369,173 B1 | 4/2002 | Kim et al. | |
| 2004/0116749 A1 | 6/2004 | Levin et al. | |
| 2007/0118004 A1 | 5/2007 | Tsuji et al. | |
| 2011/0306800 A1 * | 12/2011 | Keenan | C07C 45/53 585/323 |
| 2012/0178879 A1 | 7/2012 | Mignon et al. | |
| 2017/0226036 A1 | 8/2017 | Nelson et al. | |
| 2017/0226056 A1 | 8/2017 | Nelson et al. | |
| 2019/0256444 A1 | 8/2019 | Xu et al. | |
| 2020/0199040 A1 | 6/2020 | Ye et al. | |

FOREIGN PATENT DOCUMENTS

| | | | |
|---|---|---|---|
| JP | 06-293682 A | 10/1994 | |
| JP | 2004-292335 A | 10/2004 | |
| JP | 2020-521622 A | 7/2020 | |
| JP | 2020-521753 A | 7/2020 | |
| KR | 10-0349071 B1 | 8/2002 | |
| KR | 10-2005-0088178 A | 9/2005 | |
| KR | 10-2012-0059875 A | 6/2012 | |
| KR | 10-1367064 B1 | 2/2014 | |
| KR | 10-2017-0039744 A | 4/2017 | |
| KR | 10-1804596 B1 | 11/2017 | |
| RU | 2565764 C1 | 10/2015 | |
| WO | 2013/011156 A2 | 1/2013 | |
| WO | WO-2016020897 A1 * | 2/2016 | B01J 10/007 |
| WO | 2019-199518 A1 | 10/2019 | |

* cited by examiner

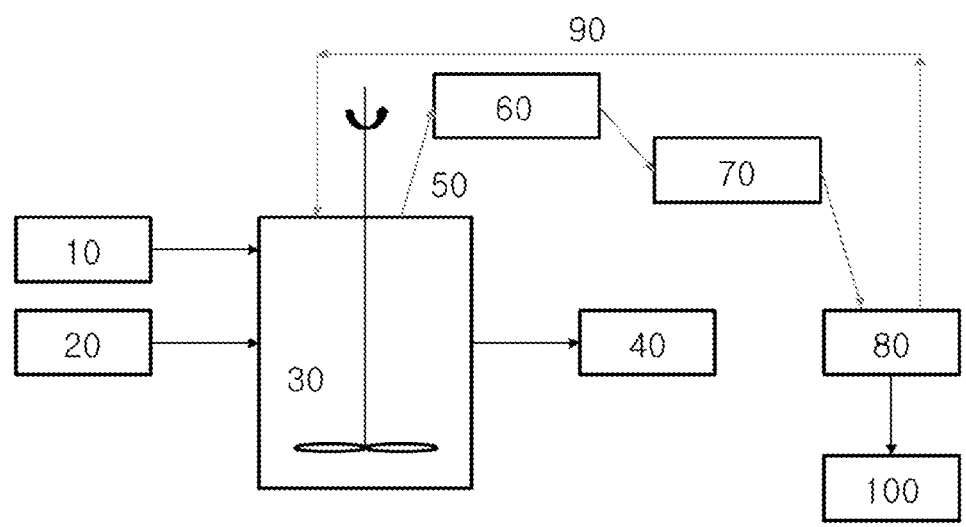

METHOD FOR PREPARING ALPHA-METHYLSTYRENE

CROSS-REFERENCE TO RELATED APPLICATIONS

This application is a National Phase entry pursuant to 35 U.S.C. § 371 of International Application No. PCT/KR2021/011611, filed on Aug. 30, 2021, and claims priority to and the benefits of Korean Patent Application No. 10-2020-0179516, filed on Dec. 21, 2020, the entire contents of which are incorporated by reference in their entirety for all purposes as if fully set forth herein.

TECHNICAL FIELD

The present application relates to a method for preparing alpha-methylstyrene.

BACKGROUND ART

Alpha-methylstyrene (AMS) is diversely used as an additive in the preparation of specific copolymers such as ABS (acrylonitrile butadiene styrene copolymer), and novel polymers.

Such alpha-methylstyrene is produced as a by-product of a phenol manufacturing process, and phenol and alpha-methylstyrene are generally prepared through oxidation and cleavage processes using cumene as a raw material. More specifically, existing alpha-methylstyrene is prepared as a by-product of a cleavage reaction of cumene peroxide under an acid catalyst. This is dimethylbenzyl alcohol (DMBA) comprised in the cumene peroxide reactant being converted to alpha-methylstyrene and water.

However, an existing method for preparing alpha-methylstyrene has problems in that, since alpha-methylstyrene is produced as a by-product of a phenol manufacturing process, the produced amount is small and a yield of the produced alpha-methylstyrene is only about 70% to 80%.

Accordingly, studies on a method for preparing alpha-methylstyrene capable of increasing a yield of the prepared alpha-methylstyrene have been required in the art.

DISCLOSURE

Technical Problem

The present application is directed to providing a method for preparing alpha-methylstyrene.

Technical Solution

One embodiment of the present application provides a method for preparing alpha-methylstyrene, the method comprising dehydrating a dimethylbenzyl alcohol solution in a reactor under an acid catalyst to prepare alpha-methylstyrene, wherein a reaction product after the dehydration reaction comprises a first reaction product comprising first alpha-methylstyrene; and a second reaction product comprising vapor ($H_2O$), second alpha-methylstyrene and unreacted materials, a temperature inside the reactor during the dehydration reaction is 135° C. or higher, a content of the acid catalyst is from 100 ppm to 1,500 ppm based on a total weight of dimethylbenzyl alcohol of the dimethylbenzyl alcohol solution, and the method comprising, after separating the second reaction product from the reactor, separating the second alpha-methylstyrene and the unreacted materials comprised in the second reaction product and recirculating the second alpha-methylstyrene and the unreacted materials to the reactor.

Advantageous Effects

A method for preparing alpha-methylstyrene according to one embodiment of the present application is capable of enhancing selectivity of the prepared alpha-methylstyrene, and increasing a yield of the prepared alpha-methylstyrene.

DESCRIPTION OF DRAWINGS

FIG. 1 is a diagram schematically illustrating a process of a method for preparing alpha-methylstyrene according to one embodiment of the present application.

REFERENCE NUMERAL

10: Acid Catalyst
20: Dimethylbenzyl Alcohol Solution
30: Reactor
40: Alpha-Methylstyrene and Unreacted Materials
50: Second Reaction Product
60: Distillation Column
70: Condenser
80: Trap
90: Second Alpha-Methylstyrene and Unreacted Materials
100: Water ($H_2O$)

DETAILED DESCRIPTION

Hereinafter, the present application will be described in more detail.

In the present specification, a description of a certain member being placed "on" another member comprises not only a case of the certain member being in contact with the another member but a case of still another member being present between the two members.

In the present specification, a description of a certain part "comprising" certain constituents means capable of further comprising other constituents, and does not exclude other constituents unless particularly stated on the contrary.

The method for preparing alpha-methylstyrene according to one embodiment of the present application comprises dehydrating a dimethylbenzyl alcohol solution in a reactor under an acid catalyst to prepare alpha-methylstyrene, wherein a reaction product after the dehydration reaction comprises a first reaction product comprising first alpha-methylstyrene; and a second reaction product comprising vapor ($H_2O$), second alpha-methylstyrene and unreacted materials, and after separating the second reaction product from the reactor, separating the second alpha-methylstyrene and the unreacted materials comprised in the second reaction product and recirculating the second alpha-methylstyrene and the unreacted materials to the reactor, a temperature inside the reactor during the dehydration reaction is 135° C. or higher, and a content of the acid catalyst is from 100 ppm to 1,500 ppm based on a total weight of dimethylbenzyl alcohol of the dimethylbenzyl alcohol solution.

The method for preparing alpha-methylstyrene according to one embodiment of the present application comprises dehydrating a dimethylbenzyl alcohol solution in a reactor under an acid catalyst to prepare alpha-methylstyrene.

As described above, alpha-methylstyrene has been prepared as a by-product of a phenol manufacturing process in the art by preparing phenol and alpha-methylstyrene through oxidation and cleavage processes using cumene as a raw material. More specifically, in the art, cumene, a starting material, is oxidized to prepare a mixture of cumene peroxide and cumyl alcohol, and the mixture of cumene peroxide and cumyl alcohol goes through a cleavage reaction to prepare phenol and acetone from the cumene peroxide and prepare alpha-methylstyrene from the cumyl alcohol. However, such an existing technology is mainly aimed at producing phenol from cumene, and since the alpha-methylstyrene is produced as a by-product of a phenol manufacturing process, there are problems in that the produced amount is small and a yield of the produced alpha-methylstyrene is only about 70% to 80%.

However, unlike the above-described existing technology of oxidizing cumene to prepare a mixture of cumene peroxide and cumyl alcohol and then preparing alpha-methylstyrene therefrom through an additional reaction, the method for preparing alpha-methylstyrene according to one embodiment of the present application prepares alpha-methylstyrene by directly dehydrating a dimethylbenzyl alcohol solution, and as a result, selectivity of the alpha-methylstyrene may be enhanced as well as increasing a yield of the alpha-methylstyrene.

In one embodiment of the present application, the acid catalyst may be a liquid acid catalyst or a solid acid catalyst. The liquid acid catalyst may be hydrochloric acid, sulfuric acid or nitric acid, and is more preferably sulfuric acid. In addition, the solid acid catalyst may be selected from among Group 4 metal oxides modified by Group 6 metal oxides, sulfated transition metal oxides, mixed metal oxides of cerium oxide and Group 4 metal oxides, and mixtures thereof.

In one embodiment of the present application, a content of the acid catalyst may be from 100 ppm to 1,500 ppm, and may be from 150 ppm to 500 ppm based on a total weight of dimethylbenzyl alcohol of the dimethylbenzyl alcohol solution. When the content of the acid catalyst is greater than 1,500 ppm based on a total weight of dimethylbenzyl alcohol of the dimethylbenzyl alcohol solution, the produced alpha-methylstyrene may be converted to an alpha-methylstyrene dimer form reducing a yield of the alpha-methylstyrene. In addition, the content of the acid catalyst being less than 100 ppm based on a total weight of dimethylbenzyl alcohol of the dimethylbenzyl alcohol solution is not preferred as well since the yield of the alpha-methylstyrene may decrease.

In one embodiment of the present application, a content of the dimethylbenzyl alcohol in the dimethylbenzyl alcohol solution may be from 8% by weight to 90% by weight, and may be from 20% by weight to 35% by weight. When the content of dimethylbenzyl alcohol is less than 8% by weight or greater than 90% by weight in the dimethylbenzyl alcohol solution, the reaction time for preparing the alpha-methylstyrene increases, and the residence time of the reactants in the reactor may increase. When the residence time of the reactants in the reactor increases as above, a side reaction of converting the alpha-methylstyrene to an alpha-methylstyrene dimer occurs more, which may lower a yield of the alpha-methylstyrene. In addition, there may be a problem of increasing a content of the acid catalyst introduced to reduce the residence time. In addition, the side reaction of converting the alpha-methylstyrene to an alpha-methylstyrene dimer may be further accelerated when an alcohol is present, and therefore, a problem of reducing selectivity of the alpha-methylstyrene may occur when the content of the dimethylbenzyl alcohol is excessively high.

The dimethylbenzyl alcohol solution may comprise, in addition to dimethylbenzyl alcohol, acetophenone, cumyl hydroperoxide, alpha-methylstyrene, cumene, dicumyl peroxide, an alpha-methylstyrene dimer, water and the like.

In one embodiment of the present application, the dimethylbenzyl alcohol solution may comprise dimethylbenzyl alcohol in 28.6% by weight, acetophenone in 0.2% by weight, cumyl hydroperoxide in 1.0% by weight, alpha-methylstyrene in 0.01% by weight, cumene in 67.0% by weight, dicumyl peroxide in 0.2% by weight, an alpha-methylstyrene dimer in 0.02% by weight and water in 2.97% by weight, based on a total weight of the dimethylbenzyl alcohol solution, however, the content is not limited thereto.

In one embodiment of the present application, the reaction product after the dehydration reaction comprises a first reaction product comprising first alpha-methylstyrene; and a second reaction product comprising vapor ($H_2O$), second alpha-methylstyrene and unreacted materials. Water is produced when the dimethylbenzyl alcohol is converted to the alpha-methylstyrene through the dehydration reaction, and by an inner temperature of the reactor, the water, some of the alpha-methylstyrene and the unreacted materials evaporate together. In other words, in one embodiment of the present application, the second reaction product represents the water, some of the alpha-methylstyrene and the unreacted materials evaporating together by an inner temperature of the reactor. In one embodiment of the present application, in order to enhance the yield of the prepared alpha-methylstyrene, water is removed from the second reaction product comprising second alpha-methylstyrene and unreacted materials evaporating with the water, and the second alpha-methylstyrene and the unreacted materials are recirculated to the reactor.

In one embodiment of the present application, the unreacted materials may comprise an unreacted dimethylbenzyl alcohol solution, the acid catalyst and the like.

In one embodiment of the present application, the method of separating the second alpha-methylstyrene and the unreacted materials comprised in the second reaction product may comprise processes of separating the second reaction product comprising vapor ($H_2O$), the second alpha-methylstyrene and the unreacted materials from the reactor, and then introducing the second reaction product to a distillation column and a condenser sequentially.

As the distillation column, distillation columns used in the art may be used. As the distillation column, a single distillation column may be used, and using the single distillation column, the second reaction product may be transferred to the condenser to describe later.

As the condenser, condensers used in the art may be used. Examples thereof may comprise a water-cooled condenser, an air-cooled condenser, an evaporative condenser and the like, but are not limited thereto. Inside the condenser may satisfy a temperature of 0° C. to 50° C., preferably 0° C. to 20° C., and a pressure of 0.1 kgf/cm$^2$ to 1.0 kgf/cm$^2$, however, the temperature and the pressure are not limited thereto.

By the processes of separating the second reaction product from the reactor and introducing the second reaction product to a distillation column and a condenser sequentially, the liquefied second alpha-methylstyrene and unreacted materials, and the water are divided into two levels in a trap. In addition, the water may be separated apart, and the second alpha-methylstyrene and the unreacted materials may be recirculated to the reactor.

In one embodiment of the present application, the temperature inside the reactor may be 135° C. or higher, may be 138° C. or higher, and 150° C. or lower during the dehydration reaction. When the temperature inside the reactor is lower than 135° C. during the dehydration reaction, the dehydration reaction, which is an endothermic reaction, may not be readily conducted. In addition, when the temperature inside the reactor is higher than 150° C. during the dehydration reaction, evaporation of cumene may increase since cumene and alpha-methylstyrene have boiling points of 152.4° C. and 166° C., respectively, and an effect of increasing the acid catalyst concentration inside the reactor may reduce a yield of the alpha-methylstyrene.

In one embodiment of the present application, the pressure inside the reactor may be from 400 torr to 700 torr, and may be from 450 torr to 650 torr during the dehydration reaction. When the pressure inside the reactor decreases during the dehydration reaction, boiling points of the reactants and the products decrease, and alpha-methylstyrene and unreacted materials evaporating to the distillation column may increase. This leads to an effect of increasing the acid catalyst concentration in the reactor relatively increasing the amount of alpha-methylstyrene converted to an alpha-methylstyrene dimer, and a yield of the alpha-methylstyrene may decrease. Accordingly, the yield of the produced alpha-methylstyrene may be enhanced when satisfying the above-described pressure inside the reactor during the dehydration reaction.

In one embodiment of the present application, the reactor is a continuous stirred tank reactor (CSTR), and the dehydration reaction may be conducted for 15 minutes to 60 minutes, and may be conducted for 25 minutes to 50 minutes. When the residence time in the reactor increases, the reaction of converting alpha-methylstyrene to an alpha-methylstyrene dimer occurs more, which may reduce a yield of the alpha-methylstyrene, and an amount of the alpha-methylstyrene produced within the same time period may decrease. Accordingly, the yield of the produced alpha-methylstyrene may be enhanced when satisfying the above-described time during which the dehydration reaction is conducted.

In one embodiment of the present application, the method for preparing alpha-methylstyrene may further comprise separating the first reaction product comprising first alpha-methylstyrene and the recirculated second alpha-methylstyrene and unreacted materials from the reactor.

A process diagram of the method for preparing alpha-methylstyrene according to one embodiment of the present application is schematically illustrated in FIG. 1. As illustrated in FIG. 1, the method for preparing alpha-methylstyrene according to one embodiment of the present application comprises dehydrating a dimethylbenzyl alcohol solution (20) in a reactor (30) under an acid catalyst (10) to prepare alpha-methylstyrene, wherein a reaction product after the dehydration reaction comprises a first reaction product comprising first alpha-methylstyrene; and a second reaction product (50) comprising vapor (H$_2$O), second alpha-methylstyrene and unreacted materials, a temperature inside the reactor (30) during the dehydration reaction is 135° C. or higher, and the method comprises, after separating the second reaction product (50) from the reactor (30), separating the second alpha-methylstyrene and the unreacted materials (90) comprised in the second reaction product (50), and recirculating the second alpha-methylstyrene and the unreacted materials (90) to the reactor (30). In addition, the method of separating the second alpha-methylstyrene and the unreacted materials (90) comprised in the second reaction product (50) may comprise processes of separating the second reaction product (50) comprising vapor (H$_2$O), the second alpha-methylstyrene and the unreacted materials from the reactor (30), and then introducing the second reaction product (50) to a distillation column (60) and a condenser (70) sequentially.

The method for preparing alpha-methylstyrene according to one embodiment of the present application is capable of enhancing a conversion ratio of dimethylbenzyl alcohol, and capable of increasing a yield of the prepared alpha-methylstyrene.

Hereinafter, the present application will be described in detail with reference to examples in order to specifically describe the present application. However, examples according to the present application may be modified to various different forms, and the scope of the present application is not construed as being limited to the examples described below. Examples of the present application are provided in order to more fully describe the present application to those having average knowledge in the art.

EXAMPLE

Example 1

To a continuous stirred tank reactor (CSTR), a dimethylbenzyl alcohol solution (300 g) and sulfuric acid (0.0225 g) were introduced. As the dimethylbenzyl alcohol solution, a solution comprising dimethylbenzyl alcohol in 28.6% by weight, acetophenone in 0.2% by weight, cumyl hydroperoxide in 1.0% by weight, alpha-methylstyrene in 0.01% by weight, cumene in 67.0% by weight, dicumyl peroxide in 0.2% by weight, an alpha-methylstyrene dimer in 0.02% by weight and water in 2.97% by weight was used. A content of the sulfuric acid was approximately 262 ppm based on a total weight of the dimethylbenzyl alcohol of the dimethylbenzyl alcohol solution.

A residence time of 30 minutes in the reactor was used as a standard, and the reactant was introduced at 10 g/min and the sulfuric acid was introduced at 0.00075 g/min to conduct a dehydration reaction. Herein, a temperature inside the reactor was 140.4° C., a pressure inside the reactor was 550 torr, and a stirring rate of the reactor was 450 rpm.

As in the process diagram of FIG. 1, a second reaction product comprising vapor (H$_2$O), second alpha-methylstyrene and unreacted materials was separated from the reactor at 1.17 ml/min, and introduced to a distillation column and a condenser sequentially. A temperature of the distillation column was 94.5° C., and a temperature of the condenser was 5° C. The second alpha-methylstyrene and the unreacted materials separated through the condenser were recirculated to the reactor at 0.68 ml/min.

In addition, as in reference numeral 40 of the process diagram of FIG. 1, a reaction product comprising alpha-methylstyrene and unreacted materials was released from the reactor at 9.5 g/min.

Example 2

A process was conducted in the same manner as in Example 1 except that the temperature inside the reactor was adjusted to 140.8° C., and the pressure inside the reactor was adjusted to 650 torr.

Herein, a flow rate of the second reaction product separated from the reactor was 0.95 ml/min, a flow rate of the second alpha-methylstyrene and the unreacted materials recirculated to the reactor was 0.55 ml/min, and a released amount of the final reaction product was 9.6 g/min.

Comparative Example 1

A process was conducted in the same manner as in Example 1 except that the temperature inside the reactor was adjusted to 128.5° C.

Herein, a flow rate of the second reaction product separated from the reactor was 0.7 ml/min, a flow rate of the second alpha-methylstyrene and the unreacted materials recirculated to the reactor was 0.5 ml/min, and a released amount of the final reaction product was 9.8 g/min.

Comparative Example 2

A process was conducted in the same manner as in Example 1 except that the temperature inside the reactor was adjusted to 133.4° C.

Herein, a flow rate of the second reaction product separated from the reactor was 1.50 ml/min, a flow rate of the second alpha-methylstyrene and the unreacted materials recirculated to the reactor was 1.17 ml/min, and a released amount of the final reaction product was 9.7 g/min.

Comparative Example 3

A process was conducted in the same manner as in Example 1 except that the temperature inside the reactor was adjusted to 137.2° C., and the introduced amount of the sulfuric acid was adjusted to 0.00572 g/min. A content of the sulfuric acid was approximately 2,000 ppm based on a total weight of the dimethylbenzyl alcohol of the dimethylbenzyl alcohol solution.

Herein, a flow rate of the second reaction product separated from the reactor was 1.03 ml/min, a flow rate of the second alpha-methylstyrene and the unreacted materials recirculated to the reactor was 0.65 ml/min, and a released amount of the final reaction product was 9.6 g/min.

Comparative Example 4

A process was conducted in the same manner as in Example 1 except that the temperature inside the reactor was adjusted to 128° C., the introduced amount of the sulfuric acid was adjusted to 0.002808 g/min, and a dimethylbenzyl alcohol solution (solution comprising dimethylbenzyl alcohol in 93.6% by weight, cumyl hydroperoxide in 0.84% by weight, cumene in 3.42% by weight, dicumyl peroxide in 0.89% by weight, an alpha-methylstyrene dimer in 0.39% by weight and water in 0.86% by weight) was used. A content of the sulfuric acid was approximately 300 ppm based on a total weight of the dimethylbenzyl alcohol of the dimethylbenzyl alcohol solution.

Herein, a flow rate of the second reaction product separated from the reactor was 0.74 ml/min, a flow rate of the second alpha-methylstyrene and the unreacted materials recirculated to the reactor was 0.41 ml/min, and a released amount of the final reaction product was 9.7 g/min.

Comparative Example 5

A process was conducted in the same manner as in Example 1 except that the temperature inside the reactor was adjusted to 135° C., the introduced amount of the sulfuric acid was adjusted to 0.000858 g/min, and the process of recirculating the second alpha-methylstyrene and the unreacted materials was not comprised. A content of the sulfuric acid was approximately 300 ppm based on a total weight of the dimethylbenzyl alcohol of the dimethylbenzyl alcohol solution.

Experimental Example

Each of the reaction products comprising alpha-methylstyrene prepared in the examples and the comparative examples was analyzed, and the results are shown in the following Table 1. The reaction product comprising alpha-methylstyrene was analyzed by high-performance liquid chromatography (HPLC).

Condition of HPLC Analysis

Column: Lichrosorb RP-18 (4.6 m×0.2 mm×10 μm) and Guard column
Eluent: mobile phase A/mobile phase B=97/3 (v/v, %) to 3 minutes
mobile phase A/mobile phase B=10/90 (v/v, %) from 3 minutes to 24 minutes
mobile phase A/mobile phase B=97/3 (v/v, %) from 24 minutes to 30 minutes
Flow rate: 1 mL/min
Column temperature: 40° C.
Run time: 30 min
Injection volume: 10 μl In the present application, the 'yield (%)' is defined as a value obtained by dividing the number of moles of alpha-methylstyrene, a product, by the number of moles of dimethylbenzyl alcohol, a raw material. For example, the yield may be represented by the following equation.

Yield(%)=[(number of moles of produced alpha-methylstyrene)/(number of moles of supplied dimethylbenzyl alcohol)]×100

In the present application, the 'conversion ratio (%)' refers to a ratio of a reactant converting to a product, and for example, the conversion ratio of dimethylbenzyl alcohol may be represented by the following equation.

Conversion ratio(%)=[(number of moles of reacted dimethylbenzyl alcohol)/(number of moles of supplied dimethylbenzyl alcohol)]×100

In the present application, the 'selectivity (%)' is defined as a value obtained by dividing the amount of change in alpha-methylstyrene by the amount of change in dimethylbenzyl alcohol. For example, the selectivity may be represented by the following equation.

Selectivity(%)=[(number of moles of produced alpha-methylstyrene)/(number of moles of reacted dimethylbenzyl alcohol)]×100

TABLE 1

|  | DMBA Conversion Ratio (%) | Alpha-Methylstyrene Selectivity (%) | Alpha-Methylstyrene Yield (%) |
| --- | --- | --- | --- |
| Example 1 | 97.9 | 99.7 | 97.6 |
| Example 2 | 96.8 | 100.2 | 97.0 |
| Comparative Example 1 | 95.9 | 98.0 | 94.0 |
| Comparative Example 2 | 95.7 | 98.3 | 94.1 |
| Comparative Example 3 | 99.53 | 91.06 | 90.63 |
| Comparative Example 4 | 99.66 | 85.02 | 84.73 |

TABLE 1-continued

|  | DMBA Conversion Ratio (%) | Alpha-Methylstyrene Selectivity (%) | Alpha-Methylstyrene Yield (%) |
|---|---|---|---|
| Comparative Example 5 | 99.79 | 87.87 | 87.69 |

Cumyl hydroperoxide comprised in the dimethylbenzyl alcohol solution may produce dimethylbenzyl alcohol and oxygen under a sulfuric acid catalyst, and the dimethylbenzyl alcohol produced by the cumyl hydroperoxide may further produce alpha-methylstyrene under a sulfuric acid catalyst, and therefore, selectivity of the alpha-methylstyrene may be greater than 100% as in the result of Example 2.

As seen from the above-described results, it was identified that, when the constitutions of the method for preparing alpha-methylstyrene according to one embodiment of the present application are not satisfied, a side reaction of converting alpha-methylstyrene to an alpha-methylstyrene dimer is further accelerated reducing selectivity and yield of the alpha-methylstyrene.

Accordingly, the method for preparing alpha-methylstyrene according to one embodiment of the present application is capable of enhancing selectivity of the prepared alpha-methylstyrene, and is capable of increasing a yield of the prepared alpha-methylstyrene.

The invention claimed is:

1. A method for preparing alpha-methylstyrene, the method comprising:
   dehydrating a dimethylbenzyl alcohol solution in a reactor under an acid catalyst to prepare alpha-methylstyrene, wherein a reaction product after the dehydration reaction comprises a first reaction product comprising a first alpha-methylstyrene; and a second reaction product comprising vapor ($H_2O$), a second alpha-methylstyrene and unreacted materials; and
   separating the second alpha-methylstyrene and the unreacted materials comprised in the second reaction product and recirculating the second alpha-methylstyrene and the unreacted materials to the reactor,
   wherein a temperature inside the reactor during the dehydration reaction is 135° C. or higher, and
   wherein a content of the acid catalyst is from 100 ppm to 1,500 ppm based on a total weight of dimethylbenzyl alcohol of the dimethylbenzyl alcohol solution.

2. The method for preparing alpha-methylstyrene of claim 1, wherein the acid catalyst is hydrochloric acid, sulfuric acid or nitric acid.

3. The method for preparing alpha-methylstyrene of claim 1, wherein a content of the dimethylbenzyl alcohol in the dimethylbenzyl alcohol solution is from 8% by weight to 90% by weight.

4. The method for preparing alpha-methylstyrene of claim 1, wherein a pressure inside the reactor is from 400 torr to 700 torr during the dehydration reaction.

5. The method for preparing alpha-methylstyrene of claim 1, wherein the reactor is a continuous stirred tank reactor (CSTR), and the dehydration reaction is conducted for 15 minutes to 60 minutes.

6. The method for preparing alpha-methylstyrene of claim 1, wherein the step of separating the second alpha-methylstyrene and the unreacted materials comprised in the second reaction product comprises processes of separating the second reaction product comprising vapor ($H_2O$), the second alpha-methylstyrene and the unreacted materials from the reactor, and then introducing the second reaction product to a distillation column and a condenser sequentially.

7. The method for preparing alpha-methylstyrene of claim 1, further comprising separating the first reaction product comprising first alpha-methylstyrene and the recirculated second alpha-methylstyrene and unreacted materials from the reactor.

* * * * *